(12) United States Patent
Neelamkavil et al.

(10) Patent No.: US 9,663,527 B2
(45) Date of Patent: May 30, 2017

(54) FACTOR XIA INHIBITORS

(71) Applicant: Merck Sharp & Dohme Corp., Rahway, NJ (US)

(72) Inventors: Santhosh F. Neelamkavil, Edison, NJ (US); Scott D. Edmondson, Clark, NJ (US); Zhuyan Guo, Scotch Plains, NJ (US); Alan W. Hruza, Hackettstown, NJ (US); Zahid Hussain, Dayton, NJ (US); Charles A. Lesburg, Newton, MA (US); Remond Moningka, Jersey City, NJ (US); Anthony K. Ogawa, New Providence, NJ (US); Rudrajit Mal, Piscataway, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 15/116,659

(22) PCT Filed: Feb. 6, 2015

(86) PCT No.: PCT/US2015/014707
§ 371 (c)(1),
(2) Date: Aug. 4, 2016

(87) PCT Pub. No.: WO2015/123090
PCT Pub. Date: Aug. 20, 2015

(65) Prior Publication Data
US 2016/0347757 A1  Dec. 1, 2016

Related U.S. Application Data

(60) Provisional application No. 61/938,230, filed on Feb. 11, 2014.

(51) Int. Cl.
*C07D 487/08* (2006.01)
*C07D 471/08* (2006.01)

(52) U.S. Cl.
CPC ......... *C07D 487/08* (2013.01); *C07D 471/08* (2013.01)

(58) Field of Classification Search
None
See application file for complete search history.

(56) References Cited

U.S. PATENT DOCUMENTS

2010/0234355 A1   9/2010   Martin et al.

FOREIGN PATENT DOCUMENTS

| WO | 2013022814 A1 | 2/2013 |
| WO | 2014022766 A1 | 2/2014 |
| WO | 2015123091 A1 | 8/2015 |
| WO | 2015123093 A1 | 8/2015 |

OTHER PUBLICATIONS

International Search Report and Written Opinion of the ISA for PCT/US 15/14707 mailed Aug. 15, 2015, 8 pages.

*Primary Examiner* — Brian J Davis
(74) *Attorney, Agent, or Firm* — Nicole M. Beeler; Catherine D. Beeler

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

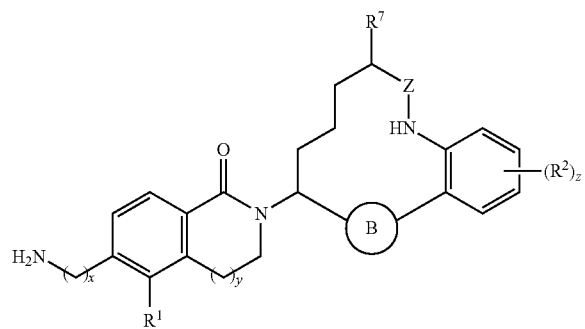

14 Claims, No Drawings

FACTOR XIa INHIBITORS

CROSS REFERENCE TO RELATED APPLICATIONS

This application is a U.S. National Phase application under 35 U.S.C. §371 of PCT Application No. PCT/US15/014707 filed Feb. 6, 2015, which claims priority from U.S. Provisional Application Ser. No. 61/938,230, filed Feb. 11, 2014.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor 25 XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo. Plasma kallikrein is a zymogen of a trypsin-like serine protease and is present in plasma. The gene structure is similar to that of factor XI. Overall, the amino acid sequence of plasma kallikrein has 58% homology to factor XI. Proteolyticactivation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Factor XIa inhibitor compounds are described in WO2013022814, WO 2013022814, WO 2013022818, WO 2013055984, WO2013056034, WO2013056060, WO2013118805. WO2013093484. WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

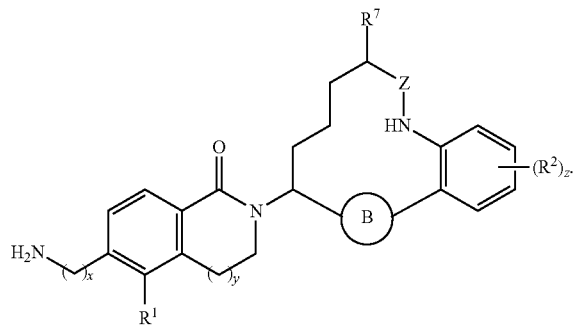

or a pharmaceutically acceptable salt thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I.

DETAILED DESCRIPTION OF THE INVENTION

The present invention relates to compounds of the following chemical formula:

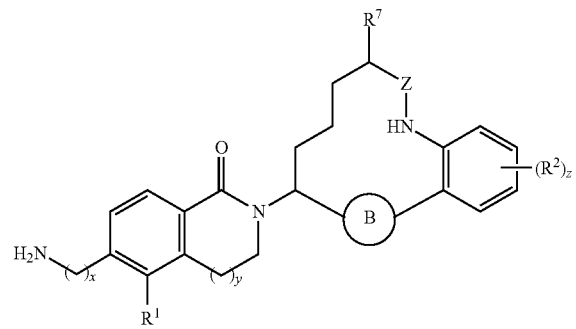

wherein

is heteroaryl, which is optionally substituted with one to three groups independently selected from the group consisting of halo, methyl and cyano;

Z is $CH_2$, $C=O$ or $CHC(O)OH$;
$R^1$ is hydrogen, $C_{1-6}$ alkyl, $C_{3-6}$ cycloalkyl, halo, cyano or hydroxy, wherein said alkyl and cycloalkyl groups are optionally substituted with one to three groups independently selected from the group consisting of halo and hydroxy;
each $R^2$ is independently selected from the group consisting of halo, cyano, hydroxy, $OR^3$, $C_{1-6}$ alkyl, $CO_2H$, $CO_2R^3$, $(R_3)CO_2H$, $(R_3)CO_2R^4$, $NR^5R^6$, $(R_3)NR^5R^6$, $NHCOR^3$, $NHC(O)OR^3$, $NHCO_2(R_3)OR^4$, $NHCO_2(R_3)CO_2H$, $(R_3)NHCO_2R^4$, $NHCONR^5R^6$, $NHSO_2R^3$, $CONR^5R^6$, $CH_2CONR^5R^6$ and $NHCONH(R_3)$heterocyclyl;
$R^3$ is hydrogen or $C_{1-6}$ alkyl, wherein said alkyl is optionally substituted with hydroxy or one to three halo;
$R^4$ is hydrogen or $C_{1-6}$ alkyl, wherein said alkyl is optionally substituted with one to three halo;
$R^5$ is hydrogen or $C_{1-6}$ alkyl,
$R^6$ is hydrogen or $C_{1-6}$ alkyl,
$R^7$ is hydrogen or $C_{1-6}$ alkyl, $CO_2H$, $COR^3$, $CONR^5R^6$, wherein said alkyl is optionally substituted with one to three halo;
x is an integer between zero and three;
y is an integer between zero and three;
z is an integer between zero and three;
or a pharmaceutically acceptable salt thereof.

In an embodiment of the invention,

is a nitrogen-containing heteroaryl, which is optionally substituted with one to three groups independently selected from the group consisting of halo, methyl and cyano. In a class of the invention,

is a selected from the group consisting of pyrrolyl, pyrazolyl, imidazolyl, triazolyl, pyridinyl, pyridazinyl, pyrimidinyl, pyrazinyl and triazinyl, wherein said groups are optionally substituted with one to three groups independently selected from the group consisting of halo, methyl and cyano. In a subclass of the invention,

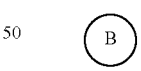

is imidazolyl. In another subclass of the invention,

is pyridinyl.

In an embodiment of the invention, Z is $CH_2$. In another embodiment of the invention, Z is $C=O$. In an embodiment of the invention, Z is $CHC(O)OH$.

In an embodiment of the invention, $R^1$ is hydrogen.

In an embodiment of the invention, $R^2$ is $NHC(O)OR^3$. In a class of the invention, $R^2$ is $NHC(O)OCH_3$. In another embodiment of the invention, $R^2$ is halo.

In an embodiment of the invention, $R^7$ is hydrogen.

In an embodiment of the invention, x is 1. In another embodiment of the invention, x is 2. In another embodiment of the invention, x is 3.

In an embodiment of the invention, y is 1. In another embodiment of the invention, y is 2. In another embodiment of the invention, y is 3.

In an embodiment of the invention, z is 0. In another embodiment of the invention, z is 1. In another embodiment of the invention, z is 2. In another embodiment of the invention, z is 3.

Reference to the preferred classes and subclasses set forth above is meant to include all combinations of particular and preferred groups unless stated otherwise.

Specific embodiments of the present invention include, but are not limited to the compounds identified herein as Examples 1 to 4, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO$^-$ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

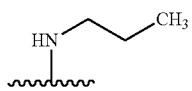

and have equivalent meanings $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic saturated aliphatic hydrocarbon group having the specified number of carbon atoms. For example, "cycloalkyl" includes cyclopropyl, cyclopropyl, cyclobutyl, cyclopentyl, cyclohexyl, and so on.

Except where noted, the term "halogen" means fluorine, chlorine, bromine or iodine.

Except where noted, the term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetrahydroquinoline. If the heteroaryl contains nitrogen atoms, it is understood that the corresponding N-oxides thereof are also encompassed by this definition.

Except where noted, the term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

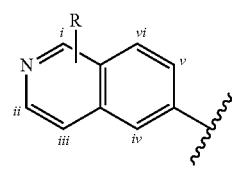

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the Factor XIa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula (I) can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TE- VETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; a stimulator of soluble guanylate cyclase (sGC), such as riociguat, vericiguat; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:

ACN is Acetonitrile; AcOH is acetic acid; atm is atmospheric pressure; aq. is aqueous; $^t$Bu is tert-butyl; $^t$BuOH is tert-butanol; Cbz is Carboxybenzyl; celite is Celite® diatomaceous earth; dba is 1,5-diphenyl-1,4-pentadien-3-one; DCE is 1,2-dichloroethane; DCM is dichloromethane; DIPEA is N,N-diisopropylethylamine; DME is dimethylether; DMF is dimethylformamide; DMP is Dess-Martin periodinane; DMS is dimethyl sulfide; dppf is 1,1'-bis(diphenylphosphino)ferrocene; EtOAc is ethyl acetate; EDC is N-(3-dimethylaminopropyl)-N'-ethylcarbodiimide hydrochloride; h is hours; HATU is 2-(1H-7-azabenzotriazol-1-yl)-1,1,3,3-tetramethyluronium hexafluorophosphate methanaminium; RP HPLC is Reverse Phase High Pressure Liquid Chromatography; Hex is hexanes; HOBt is 1-hydroxybenzotriazole; IBX is 2-iodoxybenzoic acid; LAH is lithium aluminum hydride; MeOH is methanol; MS is mass spectrum, and a mass spectrum obtained by ES-MS may be denoted herein by "ES"; m/z is mass to charge ratio; min is minutes; MP-cyanoborohydride is macroporous polymer-supported cyanoborohydride; N is normal; rt or RT is room temperature; NMP is N-methyl-2-pyrrolidone; NCS is N-chlorosuccinimide; RuPhos is 2-dicyclohexylphosphino-2',6'-diisopropoxybiphenyl; satd. is a saturated solution; SEM is 2-(trimethylsilyl)ethoxymethyl; SM is starting material; SPhos is 2-dicylohexylphosphino-2',6'-dimethoxybiphenyl; TFA is trifluoroacetic acid; THF is tetrahydrofuran; Xphos is 2-dicyclohexylphosphino-2',4',6'-triisopropylbiphenyl; TLC is thin layer chromatography; Ts is tosyl; UV is ultraviolet; W is watts; wt. % is percentage by weight; x g is times gravity; $\alpha_D$ is the specific rotation of polarized light at 589 nm; ° C. is degrees Celsius; % w/v is percentage in weight of the former agent relative to the volume of the latter agent.

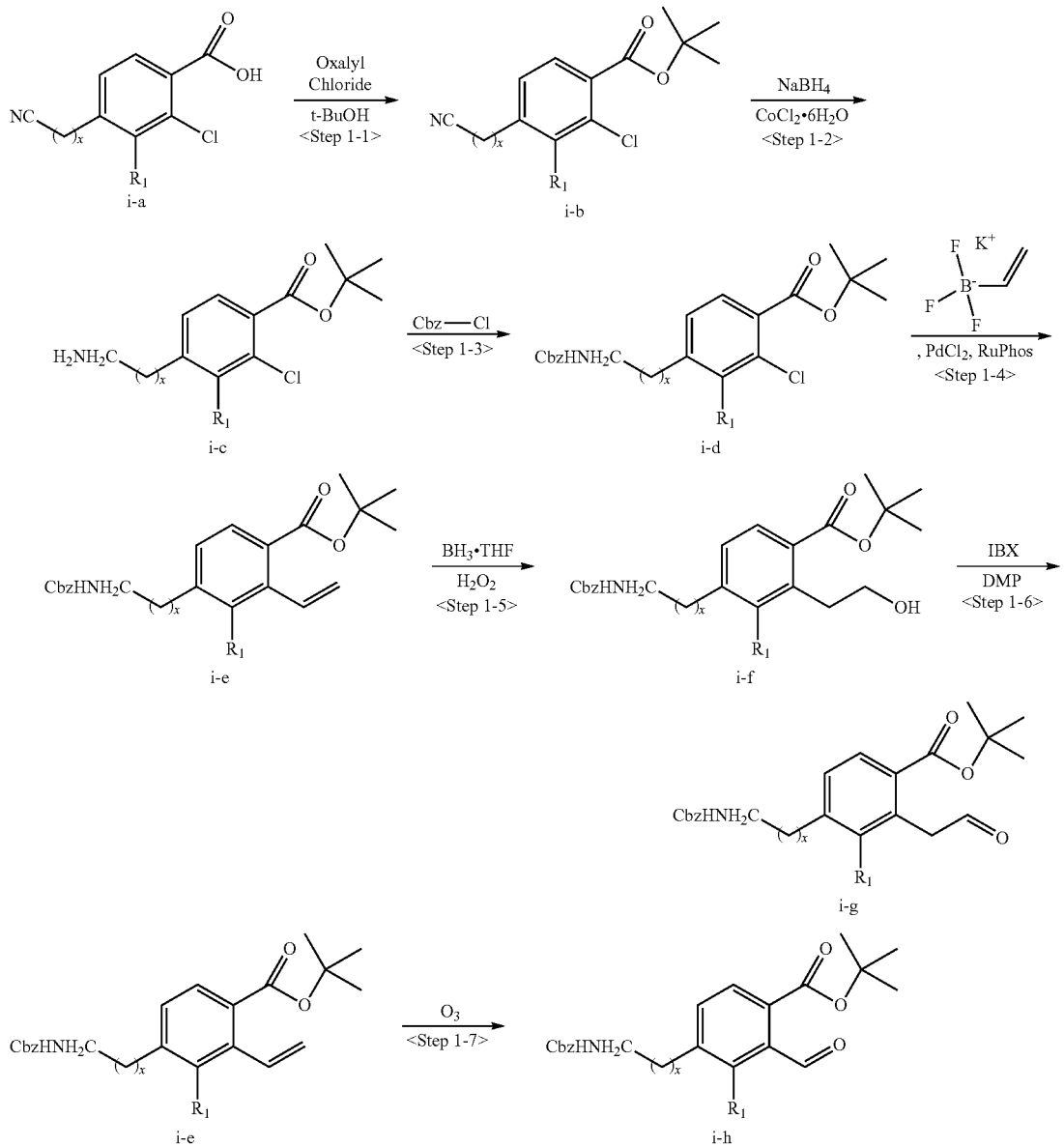

SCHEME 1

-continued
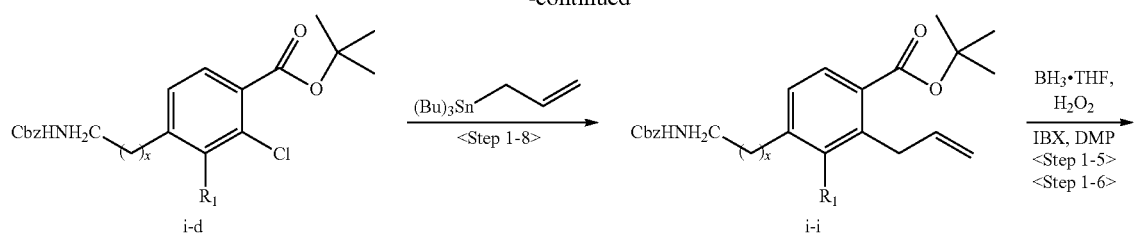
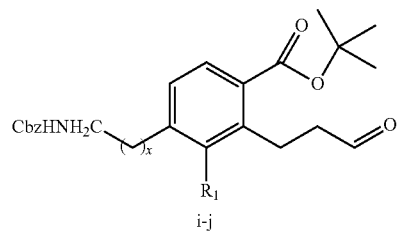
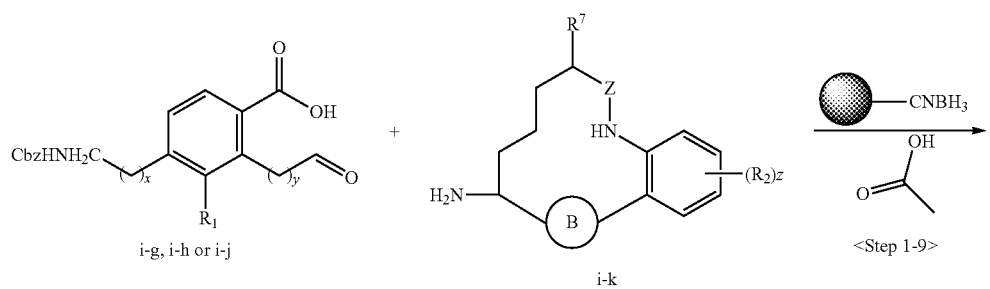
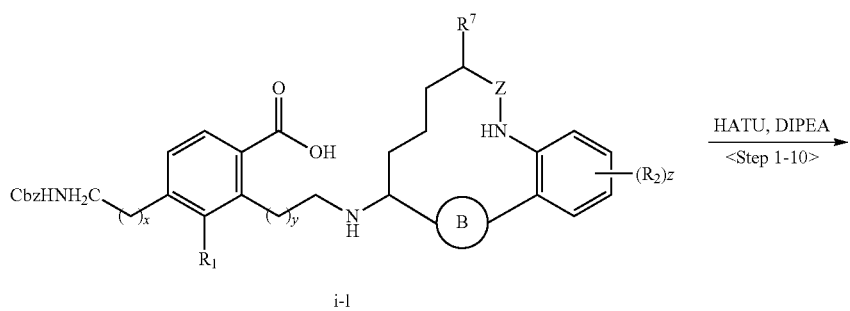
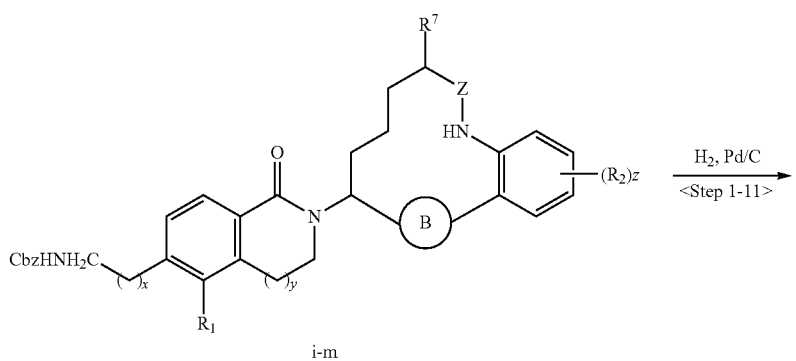

-continued

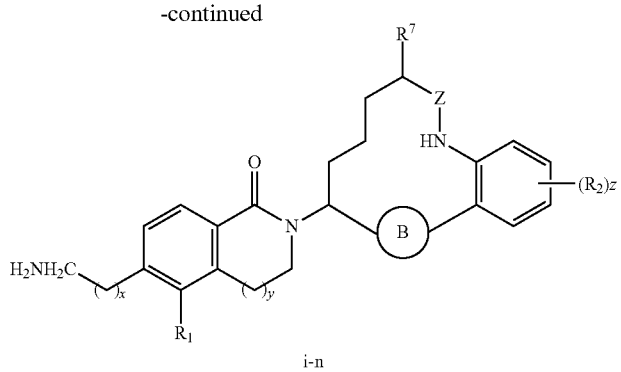

i-n

<Step 1-1>
A compound represented by formula (i-b) can be produced by allowing the suitably substituted acid (i-a) to react by a well-known process or a process similar to that described in published documents (*Organic synthesis*, pp. 8, Vol 61, 1983, Maruzen Co., Ltd., for example) in the presence of agents such as oxalyl chloride or thionyl chloride in a solvent which is inactive to the reaction, e.g., t-butanol in the presence of a catalytic amount of DMF as triethylamine or N,N-diisopropylethyl amine at a temperature in the range of 0° C. to the solvent reflux temperature.

<Step 1-2>
A compound represented by formula (i-c) can be produced by allowing the suitably substituted acid (i-b) to react by a well-known process or a process similar to that described in published documents, procedures and references (in WO1985000605, for example) in the presence of a reducing agent such as sodium borohydride in the presence of a Cobalt catalyst in a solvent which is inactive to the reaction, e.g., methanol at a temperature in the range of 0° C. to the solvent reflux temperature.

<Step 1-3>
A compound represented by formula (i-d) can be produced by allowing the suitably substituted amine (i-c) to react with a protecting agent by a well-known process or a process similar to that described in published documents (Greene, T. W., et al., *Protective Groups in Organic Synthesis* (2007), 4th Ed., for example), in the presence of protecting agents such as benzyl chloroformate in a solvent which is inactive to the reaction, e.g., THF in the presence or absence of a base such as sodium bicarbonate at a temperature in the range of 0° C. to the solvent reflux temperature.

<Step 1-4>
A compound represented by formula (i-e) can be produced by allowing the suitably substituted (i-d) to react with a coupling agent by a well-known process or a process similar to that described in published documents (Molander, G. A. et al., *Aldrichimica Acta*, 2005 and ref therein, for example), in the presence of a vinyl tetrafluoroborate salt and Palladium (II) catalyst in the presence of suitable ligands such as RuPhos, Xphos etc. in a solvent which is inactive to the reaction, e.g., THF—H$_2$O, DME, methanol etc. in the presence or absence of a base such as potassium carbonate, cesium carbonate or triethylamine in the range of 0° C. to the solvent reflux temperature.

<Step 1-5>
A compound represented by formula (i-f) can be produced by allowing the suitably substituted alkene (i-e) to react with a reducing agent followed by oxidation by a well-known process or a process similar to that described in published documents (Loudon, Marc G (2002) "Addition Reactions of Alkenes," *Organic Chemistry* (Fourth Edition ed.) New York: Oxford University Press. pp. 168-172, for example), hydroboration with BH$_3$.THF or BH$_3$.DMS in a solvent such as THF followed by oxidation with hydrogen peroxide and a base such as sodium hydroxide in water at ambient temperature.

<Step 1-6>
A compound represented by formula (i-g) can be produced by allowing the suitably substituted alcohol (i-f) to react with an oxidative agent by a well-known process or a process similar to that described in published documents (*J. Org. Chem.* 1999, Vol 64, pp 4537-4538, for example), by treating with IBX (2-iodoxybenzoic acid) and DMP (Dess-martin periodinane) in a solvent such as acetonitrile at ambient temperature.

<Step 1-7>
A compound represented by formula (i-h) can be produced by allowing the suitably substituted (i-e) to react with an oxidative agent followed by oxidation by a well-known process, or a process similar to that described in published documents (*Org. Lett.,* 2004, 3, 2835-2838, for example), ozonolysis in a ozonizer, or reacting with reagents such as potassium osmate and sodium periodate, in a solvent which is inactive to the reaction such as water:acetone mixture at ambient temperature.

<Step 1-8>
A compound represented by formula (i-i) can be produced by allowing the suitably substituted (i-d) to react with a coupling agent by a well-known process, or a process similar to that described in published documents (for example, Stille, J. K. *Angew. Chem.* 1986, Vol 98, pp 504), coupling agent such as allyltributyl tin in the presence of a Pd(0) catalyst and cesium fluoride in a solvent which is inactive to the reaction such as dioxane or toluene at a temperature in the range of 0° C. to the solvent reflux temperature.

<Step 1-9>
A compound represented by formula (i-l) can be produced by allowing the suitably substituted aldehyde (i-g, i-h or i-j) to react with a reducing agent in the presence of an amine (i-k) by a well-known process, or a process similar to that described in published documents (for example, Stuart Warren and Paul Wyatt (2008), *Organic synthesis: the disconnection approach* (2nd ed.) Oxford: Wiley-Blackwell. p. 54); by treating with sodium cyanoborohydride or sodium triacetoxyborohydride in the presence of the amine and acetic acid in a solvent which is inactive to the reaction such as methanol or chlorinated solvent, such as DCE, or a mixture of them, at a temperature in the range of 0° C., rt or the solvent reflux temperature.

<Step 1-10>

A compound represented by formula (i-o) can be produced by allowing acid (i-n) to react by a well-known process, or a process similar to that described in published documents (for example, Organic synthesis IV, Acids, amino acids, and peptides, pp. 191-309, 1992, Maruzen Co., Ltd.), in the presence of a condensing agent such as 1,3-dicyclohexyl-carbodiimide (DCC), 1-ethyl-3-(3'-dimethylaminopropyl) carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)phosphonium hexafluorophosphate (BOP reagent), or bis(2-oxo-3-oxazolidinyl)phosphinic chloride (BOP-Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

<Step 1-11>

A compound of formula (i-p) that contains a protecting group like Cbz can be deprotected following a well-known process or a process similar to that described in published documents (for example, Greene, T. W., et al., *Protective Groups in Organic Synthesis* (2007), 4th Ed.), in the presence of hydrogen gas at 1 atm pressure and with a catalyst such as Pd/C at room temperature in a solvent which is inactive to the reaction such as methanol.

SCHEME 2

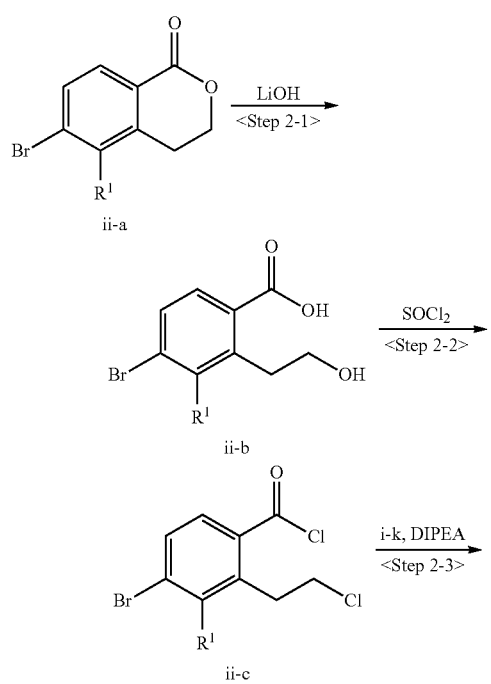

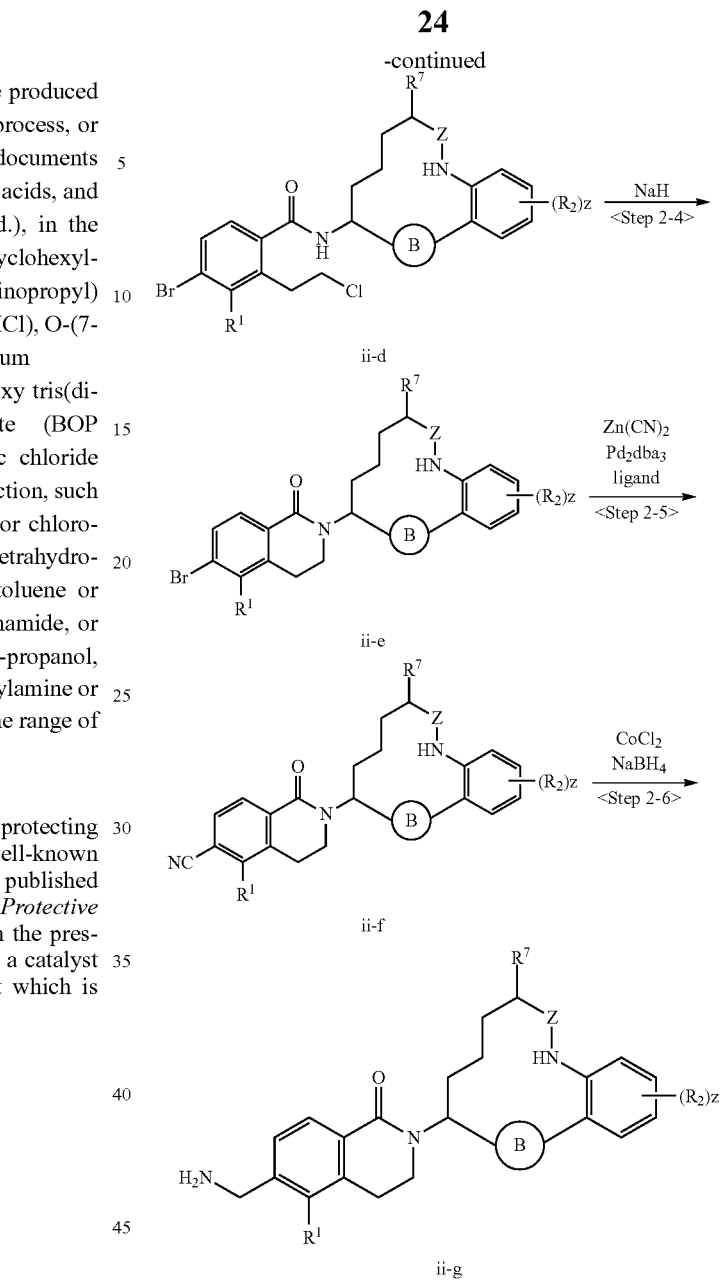

<Step 2-1>

A compound represented by formula can be prepared following procedures well known to those skilled in the art. Lactones represented by formula are allowed to react with a suitable base, such as lithium hydroxide, sodium hydroxide, or the like in multiple solvent systems, preferably a dioxane:water mixture in this example, at reaction temperatures commonly between 0° C. and rt. It should be noted that the reaction can be accelerated by heating up to the boiling temperature of the reaction mixture.

<Step 2-2>

A compound represented by formula ii-c can be prepared following a process similar to that described in published documents (WO2007/093364, page 101), in which intermediate is reacted in the presence of excess thionyl chloride. The reaction is preferably initiated at −10° C., after which, the reaction is heated to reflux for 3-24 h.

<Step 2-3>
Compounds represented by formula ii-d can be prepared by reacting intermediate ii-c with an amine, represented by i-k, in the presence of a suitable base, such as DIPEA, triethylamine or the like. The reaction is performed in a suitable inert aprotic solvent, such as DCM, THF or the like, at reaction temperatures commonly between 0° C. and rt.

<Step 2-4>
A compound represented by formula ii-e can be prepared by reacting intermediate ii-d with a suitable base, such as sodium hydride, or the like. The reaction is preferably conducted in an ethereal solvent, such as THF, at rt for 1-24 h.

<Step 2-5>
A compound represented by formula can be prepared following a process similar to that described in published documents (*Tetrahedron Lett.* 2006, 47, 3303), in which a compound represented by ii-e is reacted with a suitable cyanide donor, such as zinc cyanide, or the like. The reaction is optimally performed in the presence of a palladium catalyst and a suitable ligand, such as S-Phos, in a DMF: water mixture. The reaction is also optimally promoted by microwave heating, as described in the literature reference above.

<Step 2-6>
Compounds represented by formula ii-g can be prepared by reacting an intermediate of formula ii-f following procedures similar to those described above in <step 1-2>.

Example 1

Methyl [(7S)-7-[6-(aminomethyl)-1-oxo-3,4-dihydroisoquinolin-2(1H)-yl]-2-oxo-1,2,3,4,5,6,7,9-octahydro-11,8-(azeno)-1,9-benzodiazacyclotridecin-14-yl]carbamate

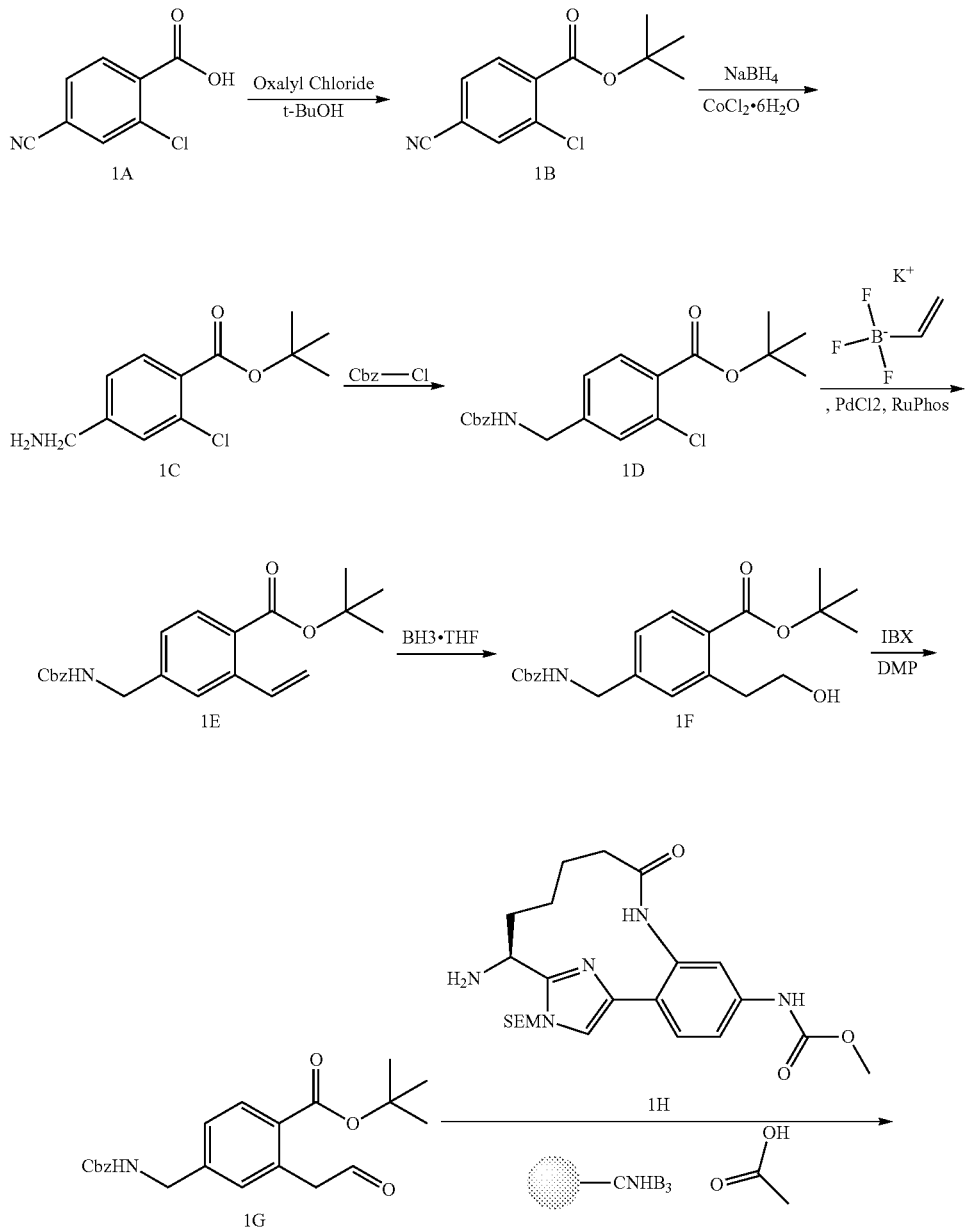

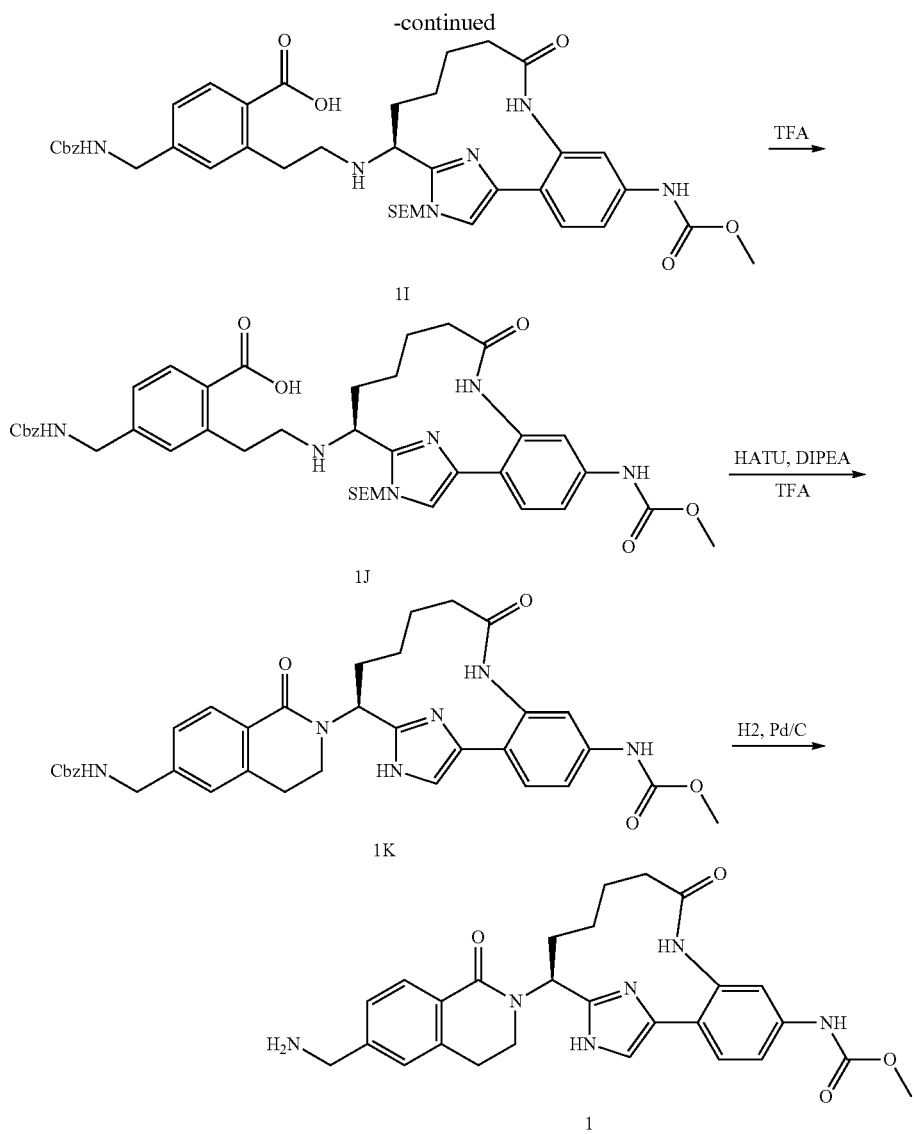

Step 1:

The commercially available 2-chloro-4-cyanobenzoic acid 1A (1.00 g, 5.51 mmol) was dissolved in dry DCM (18 ml). Oxalyl chloride (0.723 ml, 8.26 mmol) and DMF (200 µL) was added dropwise. The resulting reaction mixture was stirred at rt for 1 h, until the gas evolution was ceased. The reaction mixture was concentrated. The resulting residue was treated with pyridine (10.5 ml, 132 mmol)/t-BuOH (10.5 ml, 110 mmol) (1:1) and stirred for 6 h at rt. The solvent was evaporated under vacuum, and the residue was suspended in water. The aqueous suspension was extracted with EtOAc. The combined organic layers were washed with 1 M HCl, and the organics were dried over $Na_2SO_4$, filtered and concentrated under vacuum. The crude was purified by silica gel chromatography (0-100% EtOAc/hexanes) to give tert-butyl 2-chloro-4-cyanobenzoate 1B.

Step 2:

To the tert-butyl 2-chloro-4-cyanobenzoate 1B (1135 mg, 4.78 mmol) and cobalt(II) chloride hexahydrate (568 mg, 2.39 mmol) in MeOH (48 mL) was added $NaBH_4$ (542 mg, 14.33 mmol) cautiously. The resulting mixture was stirred at rt, and after 3 h, it was quenched by addition of concentrated HCl (0.5 mL). The mixture was stirred at 0° C. for 10 min and at rt for 45 min. Diethylenetriamine (1 mL) was then added, and the mixture was stirred for a further 15 min. The reaction mixture was filtered to removed white solids, which was washed with MeOH. The filtrate was concentrated under vacuum, and the resulting residue was dissolved in EtOAc and washed with sat aqueous $NaHCO_3$. The organics were dried over $Na_2SO_4$, filtered and concentrated under vacuum. The crude 1C was used directly in the step without further purification.

Step 3:

To the tert-butyl 4-(aminomethyl)-2-chlorobenzoate 1C (1100 mg, 4.55 mmol) and sodium bicarbonate (421 mg, 5.01 mmol) in THF (15 mL) at 0° C. was added benzyl chloroformate (0.715 mL, 5.01 mmol) dropwise. The reaction mixture was warmed to rt slowly and stirred at rt for 3 h. Water was added, and the THF was evaporated under vacuum. The residue was extracted with EtOAc, and the combined extracts were dried over $Na_2SO_4$, filtered and concentrated under vacuum. The crude was purified by silica gel chromatography (hexanes/EtOAC, 0-50%) to give tert-butyl 4-((((benzyloxy)carbonyl)amino)methyl)-2-chlorobenzoate 1D.

Step 4:

A 100-mL round bottom flask was charged with tert-butyl 4-((((benzyloxy)carbonyl)amino)methyl)-2-chlorobenzoate 1D (1460 mg, 3.88 mmol), potassium trifluoro(vinyl)borate (520 mg, 3.88 mmol), palladium(ii) chloride (69 mg, 0.388 mmol), 2-dicyclohexylphosphino-2',6'-di-i-propoxy-1,1'-biphenyl, RuPhos (544 mg, 1.165 mmol) and $Cs_2CO_3$ (3797 mg, 11.65 mmol). The flask was degassed and purged with $N_2$. To the flask was added THF (19 mL):water (2 mL), and then the reaction was heated at 85° C. overnight. After allowing to cool to rt, the reaction mixture was concentrated under vacuum, and to the residue was added EtOAc. The organic mixture was then washed with water, and the aqueous layer was extracted with EtOAc. The combined extracts were dried over $Na_2SO_4$, filtered and concentrated under vacuum. The crude was purified by silica gel chromatography (hexanes/EtOAc 0-100% gradient) to give tert-butyl 4-((((benzyloxy)carbonyl)amino)methyl)-2-vinylbenzoate 1E.

Step 5:

To a solution of tert-butyl 4-((((benzyloxy)carbonyl)amino)methyl)-2-vinylbenzoate 1E (453 mg, 1.233 mmol) in THF (15 mL) was added borane tetrahydrofuran complex (2.47 mL, 2.466 mmol) at 0° C. After removing the ice bath, the reaction mixture was stirred at rt for 4 h. Then water (2.0 mL) was added followed by 1 N NaOH (2.0 mL) and 30% hydrogen peroxide (4.4 mL). The reaction mixture was stirred at rt overnight, then cooled to 0° C., and sodium thiosulfate was added carefully. The ice bath was removed, and the mixture was stirred at rt for 30 min. The mixture was acidified to pH 3 with 1 N HCl, and extracted with EtOAc. The organic layers were dried over $Na_2SO_4$, filtered and concentrated under vacuum. The crude was purified by silica gel chromatography (hexanes/EtOAc, 0-100%) to give tert-butyl 4-((((benzyloxy)carbonyl)amino)methyl)-2-(2-hydroxyethyl)benzoate 1F. MS (ES) m/z 386.3 (M+H).

Step 6:

A suspension of tert-butyl 4-((((benzyloxy)carbonyl)amino)methyl)-2-(2-hydroxyethyl)benzoate 1F (137 mg, 0.355 mmol), IBX (119 mg, 0.427 mmol) and AcOH (24 μl, 0.427 mmol) in acetonitrile (3.0 mL) was stirred vigorously at rt overnight. A significant amount of SM was still observed by LC-MS. DMP (151 mg, 0.355 mmol) was added, and the mixture was stirred at rt for 1 h. After completion of the reaction, $NaHCO_3$ was added to the mixture. The resulting mixture was passed through a pad of celite and rinsed with EtOAc. The filtrate was concentrated under vacuum, and the residue was purified silica gel chromatography (hexanes/EtOAc, 0-100%) to give tert-butyl 4-((((benzyloxy)carbonyl)amino)methyl)-2-(2-oxoethyl)benzoate 1G.

Step 7:

tert-Butyl 4-((((benzyloxy)carbonyl)amino)methyl)-2-(2-oxoethyl)benzoate 1G (77.0 mg, 0.201 mmol) and macrocycle 1H (synthesized as in the publication WO2011/100401 A1; 30 mg, 0.059 mmol) were dissolved in MeOH (1.0 mL):DCE (1.0 mL) mixture. MP-cyanoborohydride (261 mg, 0.602 mmol) was then added followed by acetic acid (35 μl, 0.602 mmol), and the mixture was stirred at rt for 4 h. The resin was filtered, rinsed with MeOH, and the filtrate was concentrated under vacuum. The residue was dissolved in EtOAc, washed with sat aqueous $NaHCO_3$, dried over $Na_2SO_4$, filtered and concentrated under vacuum. The crude was purified by silica gel chromatography (0-100% EtOAc/hexanes) to give tert-butyl 4-({[(benzyloxy)carbonyl]amino}methyl)-2-(2-{[(7S)-14-[(methoxycarbonyl)amino]-2-oxo-9-{[2-(trimethylsilyl)ethoxy]methyl}-1,2,3,4,5,6,7,9-octahydro-11,8-(azeno)-1,9-benzodiazacyclotridecin-7-yl]amino}ethyl)benzoate 1I. MS (ES) m/z 841.8 (M+H).

Step 8:

tert-Butyl 4-({[(benzyloxy)carbonyl]amino}methyl)-2-(2-{[(7S)-14-[(methoxycarbonyl)amino]-2-oxo-9-{[2-(trimethylsilyl)ethoxy]methyl}-1,2,3,4,5,6,7,9-octahydro-11,8-(azeno)-1,9-benzodiazacyclotridecin-7-yl]amino}ethyl)benzoate 1I (100 mg, 0.119 mmol) in DCM (1.2 mL) was added TFA (500 μl, 6.49 mmol) at rt, and the reaction mixture was stirred at the same temperature for 2 h. Upon completion, water was added, and the mixture was concentrated under vacuum. The aqueous layer was extracted with EtOAc, washed with brine and the combined organic layers were dried over $Na_2SO_4$, filtered and concentrated under vacuum. The crude 1J was used directly in the next step without further purification.

Step 9:

4-({[(benzyloxy)carbonyl]amino}methyl)-2-(2-{[(7S)-14-[(methoxycarbonyl)amino]-2-oxo-9-{[2-(trimethylsilyl)ethoxy]methyl}-1,2,3,4,5,6,7,9-octahydro-11,8-(azeno)-1,9-benzodiazacyclotridecin-7-yl]amino}ethyl)benzoic acid 1J (93 mg, 0.118 mmol) and DIPEA (103 μl, 0.592 mmol) in THF (1.2 mL) was added HATU (45 mg, 0.118 mmol). The reaction mixture was stirred at rt for 1 h before concentrating under vacuum. The crude was purified by silica gel chromatography (0-100% EtOAc/hexanes) to give the amide-coupling product. The amide-coupling product in DCM (0.5 mL) was added TFA (1.0 mL), and the reaction mixture was stirred at rt for 2 h before diluting with DCM. The DCM layer was then washed with sat aqueous $NaHCO_3$, and the organic layer was dried over $Na_2SO_4$, filtered and concentrated under vacuum to give crude benzyl ({2-[(7S)-14-[(methoxycarbonyl)amino]-2-oxo-1,2,3,4,5,6,7,9-octahydro-11,8-(azeno)-1,9-benzodiazacyclotridecin-7-yl]-1-oxo-1,2,3,4-tetrahydroisoquinolin-6-yl}methyl)carbamate 1K. MS (ES) m/z 637.6 (M+H).

Step 10:

To the compound 1K (58 mg, 0.091 mmol) in MeOH (1.8 mL) was added Pd/C (6.0 mg, 0.056 mmol) in one portion. The flasked was evacuated under vacuum and purged with hydrogen (the process was repeated 3×). The heterogeneous mixture was then stirred at rt under 1 atm hydrogen for 12 h. Upon completion by LC-MS, the mixture was filtered through a pad of celite, rinsed with MeOH, and the filtrate was concentrated under vacuum. The crude was purified by RP HPLC (Gilson on a 19λ100 mm, Waters XBridge C18 column, 5μ particle size, linear gradient, standard 1% ACN/H2O to 100% ACN/H2O buffering with 0.05% TFA @ flow rate 30 mL/min over 15 min) to give methyl [(7S)-7-[6-(aminomethyl)-1-oxo-3,4-dihydroisoquinolin-2(1H)-yl]-2-oxo-1,2,3,4,5,6,7,9-octahydro-11,8-(azeno)-1,9-benzodiazacyclotridecin-14-yl]carbamate trifluoroacetate 1. MS (ES) m/z 503.5 (M+H).

Example 2

Methyl [(7S)-7-[7-(aminomethyl)-1-oxo-1,3,4,5-tetrahydro-2H-2-benzazepin-2-yl]-2-oxo-1,2,3,4,5,6,7,9-octahydro-11,8-(azeno)-1,9-benzodiazacyclotridecin-14-yl]carbamate trifluoroacetate The intermediate 1D in Step 3 was treated with allyltributyltin under well-known Stille conditions to obtain the corresponding allyl intermediate which could be treated with Steps 5 to 10 sequentially to obtain Example 2. MS (ES) m/z 517.6 (M+H).

Example 3

Methyl [(7S)-7-[5-(aminomethyl)-1-oxo-1,3-di-hydro-2H-isoindol-2-yl]-2-oxo-1,2,3,4,5,6,7,9-octa-hydro-11,8-(azeno)-1,9-benzodiazacyclotridecin-14-yl]carbamate The intermediate 1E in Step 4 was oxidized to aldehyde under standard oxidative conditions described in the literature and the aldehyde was treated with Steps 7 to 10 sequentially to obtain Example 3. MS (ES) m/z 489.43 (M+H).

Example 4

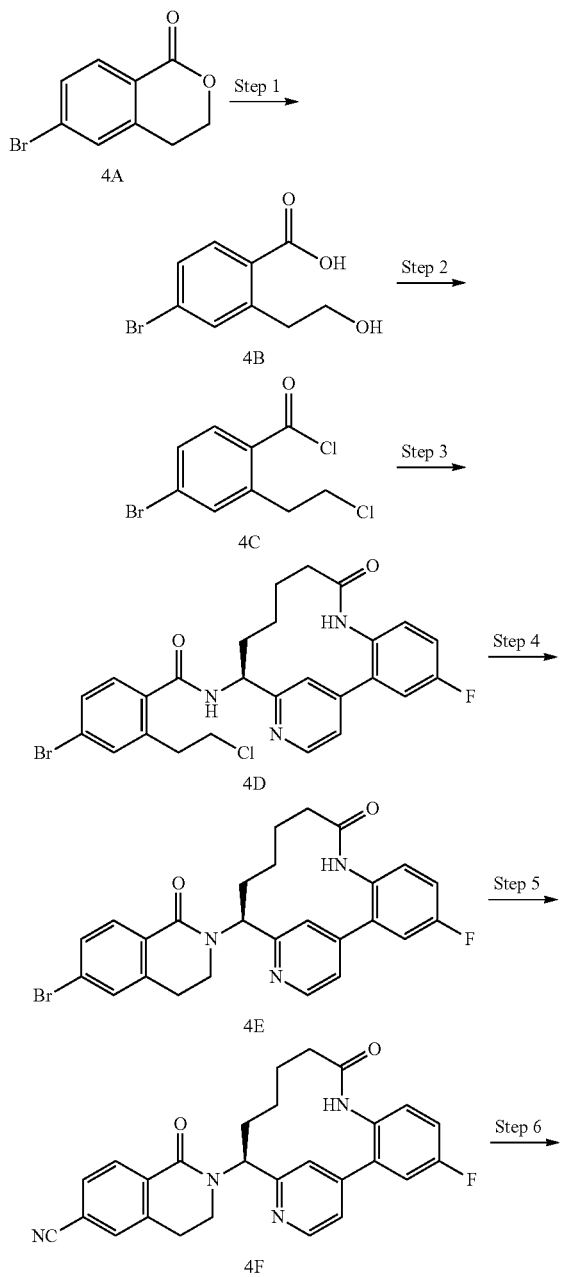

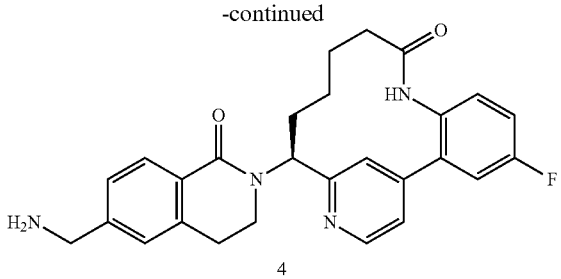

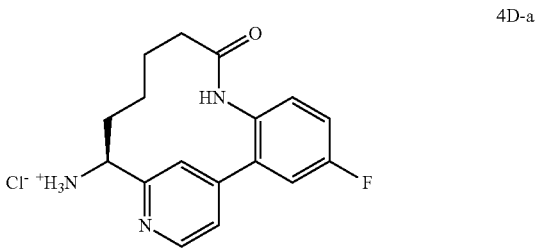 [SMILES: [Cl-] ; [NH3+][C@H]1CCCCC(=O)Nc2ccc(F)cc2-c2ccnc1c2]

Step 1:

Lithium hydroxide (1.19 g, 49.5 mmol) was added to a stirred solution of 6-bromoisochroman-1-one (4A; 1.41 g, 6.19 mmol) in a methanol:THF mixture (30 mL of a 2:3 mixture, respectively), and the reaction mixture was allowed to stir at rt. After 30 min, the reaction was quenched by the addition of 1N HCl, and the resulting mixture was extracted with EtOAc. The layers were separated, and the organic layer was dried (Na$_2$SO$_4$), filtered and concentrated to afford the title compound, 4-bromo-2-(2-hydroxyethyl)benzoic acid (4B). m/z (ES) 245 (MH)$^+$.

Step 2:

4-Bromo-2-(2-hydroxyethyl)benzoic acid (4B, 500 mg, 2.04 mmol) was added to thionyl chloride (4.0 mL) at −10° C. The reaction mixture was allowed to stir at −10° C. for 20 min, at which time, the reaction was heated to reflux. After a total of 4 h at reflux, the reaction mixture was cooled to rt and concentrated in vacuo to afford the title compound, 4-bromo-2-(2-chloroethyl)benzoyl chloride (4C).

Step 3:

A solution of 4-bromo-2-(2-chloroethyl)benzoyl chloride (545 mg, 1.93 mmol) in DCM (1.0 mL) was added to a stirred suspension of compound 4D-a (prepared following procedures described in WO2011/100401; m/z (ES) 300 (MH)$^+$; 180 mg, 0.484 mmol) and DIPEA (338 μL, 1.93 mmol) in DCM (3.0 mL), and the resulting suspension was allowed to stir at rt. After 1 h, the reaction mixture was partitioned between EtOAc and water. The layers were separated, and the organic layer was dried (Na$_2$SO$_4$), filtered and concentrated to afford a crude product that was purified by column chromatography on silica gel (isocratic elution; 15% methanol/DCM as eluent) the title compound, 4-bromo-2-(2-chloroethyl)-N-(2$^5$-fluoro-4-oxo-3-aza-1(4,2)-pyridina-2(1,2)-benzenacyclononaphane-9-yl)benzamide (4D). m/z (ES) 544 (MH)$^+$.

Step 4:

Sodium hydride (35 mg, 0.875 mmol) was added to a stirred suspension of 4-bromo-2-(2-chloroethyl)-N-(2$^5$-fluoro-4-oxo-3-aza-1(4,2)-pyridina-2(1,2)-benzenacyclononaphane-9-yl)benzamide (4D; 158 mg, 0.290 mmol) in THF (3 mL), and the resulting suspension was allowed to stir at rt. After 45 min, the reaction was quenched satd. aq. NH₄Cl, and the resulting mixture was extracted with EtOAc. The organic layer was dried (Na₂SO₄), filtered and concentrated to afford a crude product that was purified by column chromatography on silica gel (isocratic elution; 20% MeOH: DCM as eluent) the title compound, 9-(6-bromo-1-oxo-3,4-dihydroisoquinolin-2(1H)-yl)-2⁵-fluoro-3-aza-1(4,2)-pyridina-2(1,2)-benzenacyclononaphan-4-one (4E). m/z (ES) 508 (MH)⁺.

Step 5:

A microwave vial was charged with 9-(6-bromo-1-oxo-3,4-dihydroisoquinolin-2(1H)-yl)-2⁵-fluoro-3-aza-1(4,2)-pyridina-2(1,2)-benzenacyclononaphan-4-one (4E; 121 mg, 0.238 mmol), zinc cyanide (34 mg, 0.286 mmol), Pd₂dba₃ (22 mg, 0.024 mmol), SPhos (20 mg, 0.048 mmol). The solids were suspended in a DMF:water mixture (1.5 mL of a 100:1 mixture, respectively), and the resulting suspension was degassed via a stream of N₂. The vial was sealed and heated in a microwave reactor at 120° C. for 30 min. After cooling to rt, the suspension was diluted with EtOAc, and filtered through a pad of Celite®. The organics were washed with water and brine, dried (Na₂SO₄), filtered and concentrated to afford a crude product that was purified by column chromatography on silica gel (gradient elution; 0-100% [(3:1) EtOH:EtOAc]/hexanes as eluent) the title compound, 2-(2⁵-fluoro-4-oxo-3-aza-1(4,2)-pyridina-2(1,2)-benzenacyclononaphane-9-yl)-1-oxo-1,2,3,4-tetrahydroisoquinoline-6-carbonitrile (4F). m/z (ES) 455 (MH)⁺.

Step 6:

Sodium borohydride (20 mg, 0.527 mmol) was added in several portions to a stirred suspension of 2-(2⁵-fluoro-4-oxo-3-aza-1(4,2)-pyridina-2(1,2)-benzenacyclononaphane-9-yl)-1-oxo-1,2,3,4-tetrahydroisoquinoline-6-carbonitrile (4F; 51 mg, 0.112 mmol) and cobalt(II) chloride hexahydrate (20 mg, 0.84 mmol) in MeOH (1 mL). The reaction mixture was allowed to stir at rt, and after 45 min, was cooled to 0° C. and quenched by the addition of 3M HCl, and the resulting mixture was stirred at 0° C. for 10 min, followed by warming to rt over 5 min. Diethylenetriamine (180 µL) was added, and the mixture was stirred for an additional 15 min at rt, at which point, concentration in vacuo yielded the crude product, which was purified by RP HPLC (Gilson on a 19λ100 mm, Waters XBridge C18 column, 5µ particle size, linear gradient, 20% ACN/H₂O to 80% ACN/H₂O buffering with 0.05% TFA @ flow rate 30 mL/min over 15 min) to afford the title compound, 9-(6-(aminomethyl)-1-oxo-3,4-dihydroisoquinolin-2(1H)-yl)-2⁵-fluoro-3-aza-1(4,2)-pyridina-2(1,2)-benzenacyclononaphan-4-one (4). m/z (ES) 459 (MH)⁺.

| Example # | Structure | LCMS [M + H] | hFactor XIa Ki |
|---|---|---|---|
| 1 | Chiral | 503.5 | 2.4 nM |
| 2 | Chiral | 517.6 | 3.9 nM |

-continued

| Example # | Structure | LCMS [M + H] | hFactor XIa Ki |
|---|---|---|---|
| 3 | 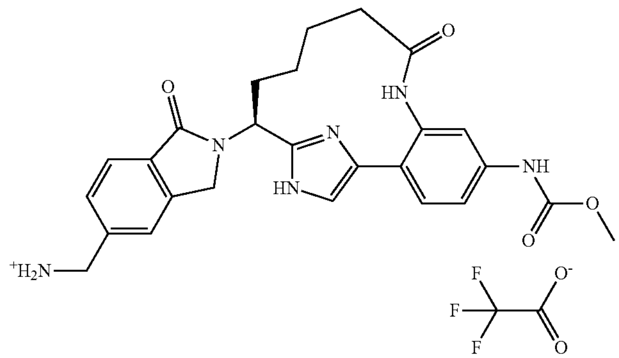 [SMILES: COC(=O)Nc1ccc2c(c1)NC(=O)CCCC[C@H](N1Cc3cc(C[NH3+])ccc3C1=O)c1nc-2c[nH]1 ; O=C([O-])C(F)(F)F] | 489.4 | 70 nM |
| 4 | 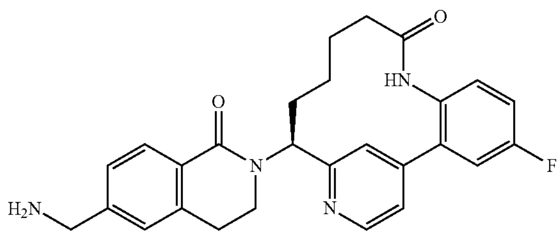 [SMILES: NCc1ccc2c(c1)CCN([C@H]1CCCCC(=O)Nc3ccc(F)cc3-c3ccnc1c3)C2=O] | 459 | 170 nM |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and the synthetic substrate, Z-Gly-Pro-Arg-AFC, TFA salt (Sigma #C0980) at a concentration of 100 µM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels

What is claimed is:
1. A compound of the formula:

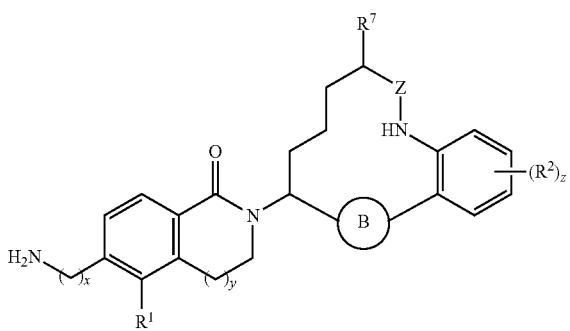

wherein

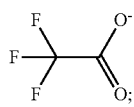

is heteroaryl, which is optionally substituted with one to three groups independently selected from the group consisting of halo, methyl and cyano;
Z is $CH_2$, $C=O$ or $CHC(O)OH$;
$R^1$ is hydrogen, $C_{1-6}$ alkyl, $C_{3-6}$ cycloalkyl, halo, cyano or hydroxy, wherein said alkyl and cycloalkyl groups are optionally substituted with one to three groups independently selected from the group consisting of halo and hydroxy;
each $R^2$ is independently selected from the group consisting of halo, cyano, hydroxy, $OR^3$, $C_{1-6}$ alkyl, $CO_2H$, $CO_2R^3$, $(R_3)CO_2H$, $(R_3)CO_2R^4$, $NR^5R^6$, $(R_3)NR^5R^6$, $NHCOR^3$, $NHC(O)OR^3$, $NHCO_2(R_3)OR^4$, $NHCO_2(R_3)CO_2H$, $(R_3)NHCO_2R^4$, $NHCONR^5R^6$, $NHSO_2R^3$, $CONR^5R^6$, $CH_2CONR^5R^6$ and $NHCONH(R_3)$heterocyclyl;
$R^3$ is hydrogen or $C_{1-6}$ alkyl, wherein said alkyl is optionally substituted with hydroxy or one to three halo;
$R^4$ is hydrogen or $C_{1-6}$ alkyl, wherein said alkyl is optionally substituted with one to three halo;
$R^5$ is hydrogen or $C_{1-6}$ alkyl,
$R^6$ is hydrogen or $C_{1-6}$ alkyl,
$R^7$ is hydrogen or $C_{1-6}$ alkyl, $CO_2H$, $COR^3$, $CONR^5R^6$, wherein said alkyl is optionally substituted with one to three halo;
x is an integer between zero and three;
y is an integer between zero and three;
z is an integer between zero and three;
or a pharmaceutically acceptable salt thereof.

2. The compound of claim 1 wherein

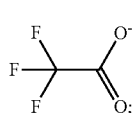

is a nitrogen-containing heteroaryl, which is optionally substituted with one to three groups independently selected from the group consisting of halo, methyl and cyano; or a pharmaceutically acceptable salt thereof.

3. The compound of claim 1 wherein

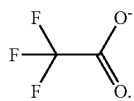

is a selected from the group consisting of pyrrolyl, pyrazolyl, imidazolyl, triazolyl, pyridinyl, pyridazinyl, pyrimidinyl, pyrazinyl and triazinyl, wherein said groups are optionally substituted with one to three groups independently selected from the group consisting of halo, methyl and cyano; or a pharmaceutically acceptable salt thereof.

4. The compound of claim 1 wherein $R^1$ is hydrogen; or a pharmaceutically acceptable salt thereof.

5. The compound of claim 1 wherein $R^2$ is $NHC(O)OR^3$; or a pharmaceutically acceptable salt thereof.

6. The compound of claim 1 wherein x is 1; or a pharmaceutically acceptable salt thereof.

7. The compound of claim 1 selected from:

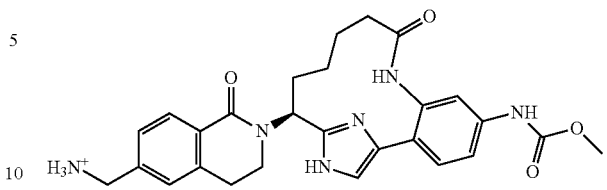

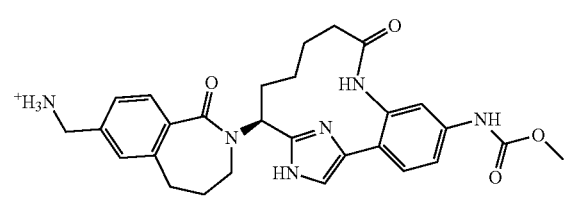

or

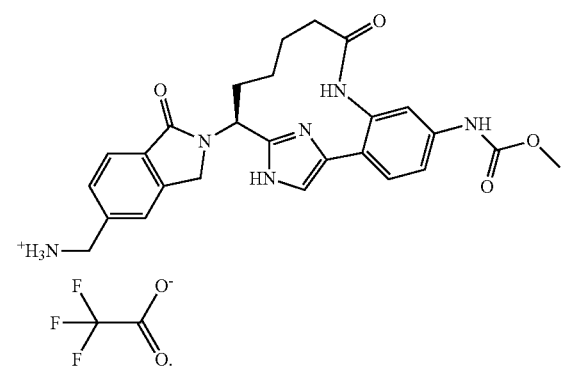

8. A pharmaceutical composition comprising a compound of claim 1 and a pharmaceutically acceptable carrier.

9. A method for inhibiting thrombus formation in blood or treating thrombus formation in blood comprising administering a composition of claim 8 to a mammal in need of thereof.

10. A method for preventing thrombus formation in blood comprising administering a composition of claim 8 to a mammal in need thereof.

11. A method of treating venous thromboembolism and pulmonary embolism in a mammal comprising administering a composition of claim 8 to a mammal in need thereof.

12. A method of treating deep vein thrombosis in a mammal comprising administering a composition of claim 8 to a mammal in need thereof.

13. A method of treating thromboembolic stroke in a human comprising administering a composition of claim 8 to a human in need thereof.

14. The compound of claim 1 which is
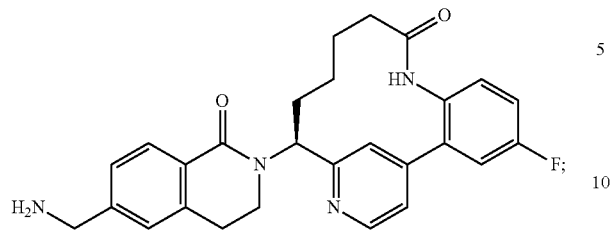
or a pharmaceutically acceptable salt thereof.
* * * * *